(12) United States Patent
Soane et al.

(10) Patent No.: US 6,306,272 B1
(45) Date of Patent: *Oct. 23, 2001

(54) METHOD AND DEVICE FOR PERFORMING CHEMICAL REACTIONS

(75) Inventors: David S. Soane; Zoya M. Soane, both of Piedmont, CA (US)

(73) Assignee: Soane Biosciences, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/172,187

(22) Filed: Oct. 13, 1998

Related U.S. Application Data

(63) Continuation of application No. 08/974,372, filed on Nov. 19, 1997, now Pat. No. 6,093,296, which is a continuation of application No. 08/615,642, filed on Mar. 13, 1996, now Pat. No. 5,750,015, which is a continuation-in-part of application No. 08/430,134, filed on Apr. 26, 1995, now abandoned, which is a continuation of application No. 08/196,763, filed on Feb. 14, 1994, now abandoned, which is a continuation of application No. 07/880,187, filed on May 7, 1992, now abandoned, which is a continuation of application No. 07/487,021, filed on Feb. 28, 1990, now Pat. No. 5,126,022.

(51) Int. Cl.⁷ .................... G01N 27/26; G01N 27/447
(52) U.S. Cl. .................... 204/451; 204/450; 204/600; 204/601
(58) Field of Search .................... 204/450, 451, 204/452, 453, 455, 600, 601, 602, 603, 604, 605

(56) References Cited

U.S. PATENT DOCUMENTS

| | | | |
|---|---|---|---|
| 4,390,403 | * | 6/1983 | Batchelder ............... 204/547 |
| 4,471,647 | | 9/1984 | Jerman et al. ............ 73/23.4 |
| 4,474,889 | | 10/1984 | Terry et al. ............. 73/23.42 X |
| 4,680,201 | | 7/1987 | Hjerten ................. 204/601 |

(List continued on next page.)

FOREIGN PATENT DOCUMENTS

| | | |
|---|---|---|
| 27 06 193 | 8/1974 | (DE) . |
| 0 307 332 | 3/1989 | (EP) . |

(List continued on next page.)

OTHER PUBLICATIONS

Anthony T. Andrews, "Electrophoresis: Theory, Techniques, and Biochemical and Clinical Applications. Chapter 8" (1986) pp. 205–240.*

Cobb et al No month available (1990) *Anal. Chem.* 82: 2478–2483.

(List continued on next page.)

*Primary Examiner*—Jill Warden
*Assistant Examiner*—John S. Starsiak, Jr.
(74) *Attorney, Agent, or Firm*—Perkins Coie LLP

(57) ABSTRACT

Devices and methods are disclosed for moving charged molecules through a medium by the application of a plurality of electrical fields of sufficient strength and applied for sufficient amounts of time so as to move the charged molecules through the medium. The devices although preferably small in size, preferably generate large numbers (100 or more) of electrical fields to a movement area which preferably contains a liquid buffered or gel medium. Mixtures of charged molecules are pulled through the gel by the force of the electrical fields. The fields are preferably activated simultaneously or sequentially one after another at various speeds to create complex force field distributions or moving field waves along the separation medium. Charged molecules capable of moving quickly through the gel will be moved along by the faster moving field waves and be separated from slower moving molecules. The fields can be activated by computer software and can be used to move molecules away from and toward each other to obtain rapid and complex chemical synthesis, sequencing or reaction protocols.

8 Claims, 2 Drawing Sheets

U.S. PATENT DOCUMENTS

| | | | |
|---|---|---|---|
| 4,740,283 | 4/1988 | Lass et al. | 204/458 |
| 4,834,862 | 5/1989 | Breiner et al. | 204/548 |
| 4,891,120 | 1/1990 | Sethi et al. | 204/600 |
| 4,908,112 | 3/1990 | Pace | 204/601 X |
| 4,911,817 | 3/1990 | Kindlmann | 204/607 |
| 4,935,040 | 6/1990 | Goedert | 73/23.22 |
| 5,126,022 | 6/1992 | Scane et al. | 204/458 |
| 5,232,565 | 8/1993 | Zare et al. | 204/452 |
| 5,630,924 | 5/1997 | Fuchs et al. | 204/601 |

FOREIGN PATENT DOCUMENTS

| | | |
|---|---|---|
| 0 361 046 | 8/1989 | (EP). |
| 0 356 187 | 2/1990 | (EP). |
| 0 376 611 | 4/1990 | (EP). |
| WO 84/02001 | 5/1984 | (WO). |
| WO 96/04547 * | 2/1996 | (WO). |

OTHER PUBLICATIONS

D. Jen Harrison et al No month available (1993) *Analytica Chimica Acta.* 283: 361–366.

Hjerten No month available (1985) *J. of Chromatography* 347: 191–198.

Thormann et al No month available (1981) *Analytical Isotachophoresis* 33–39.

Thormann et al No month available (1984) *Electrophoresis* 323–337.

* cited by examiner

METHOD AND DEVICE FOR PERFORMING CHEMICAL REACTIONS

This application is a continuation of U.S. application Ser. No. 08/974,372, filed Nov. 19, 1997, now U.S. Pat. No. 6,093,296 which is a continuation of U.S. patent application Ser. No. 615,642, filed Mar. 13, 1996, now U.S. Pat. No. 5,750,015, which is a continuation-in-part of U.S. application Ser. No. 08/430,134, filed Apr. 26, 1995, now abandoned, which is a continuation of U.S. application Ser. No. 08/196,763, filed Feb. 14, 1994, now abandoned, which is a continuation of U.S. application Ser. No. 07/880,187, filed May 7, 1992, now abandoned, which is a continuation of U.S. application Ser. No. 07/487,021, filed Feb. 28, 1990, now U.S. Pat. No. 5,126,022.

FIELD OF THE INVENTION

This invention relates generally to the fields of electrophoresis and photolithography which is applied in a manner so as to integrate technological innovations in the fields of biochemistry, polymer science, molecular genetics and electronics. More specifically, the invention relates to a method of moving charged molecules or particles in a medium by the simultaneous or sequential application of a plurality of electrical fields and devices for carrying out that method, where the supporting substrate is a substantially uncharged organic polymeric substrate and the device allows for movement along a central trench and lateral trenches.

BACKGROUND OF THE INVENTION

Electrophoresis is an analytical technique to separate and identify charged particles, ions, or molecules. It involves the imposition of an electric field to move charged species in a liquid medium. The most often studied species are biomacromolecules, such as proteins and DNA fragments, which are usually polyelectrolytes. However, electrophoresis can be used to separate any charged materials including various cells, bacteria and viral materials. At a fixed pH and ionic strength, a given polyelectrolyte acquires a certain number of net charges. Such particles are surrounded by counter-ions and have various charges, sizes (volume and shape) which affect movement. Molecules are separated by their different mobilities under an applied electric field. The mobility variation derives from the different charge and frictional resistance characteristics of the molecules. The more charged and streamlined the molecules, the faster their movement.

When a mixture containing several molecular species is introduced into an electrophoretic separation medium and an electric field is applied, the different charged components migrate at various speeds in the system leading to the resolution of the mixture. Bands appear, depending on the mobilities of the components. The exact location (thus time of emergence of the components at the end of the medium opposite to the point of introduction) depends on the interaction of the polyelectrolytes with the surrounding medium, via the influence of pH, ionic strength, ion type and whether the medium is a buffered solution of ions, polymeric solution, or gel such as a cross-linked gel. Cross-linked gels and polymeric solutions can effect separation by size or sieving. Hence, electrophoresis can be classified into two basic types including (1) free solution and (2) gel electrophoresis. The most frequently used gel media are based on polyacrylamide (known as PAGE) and agarose gels.

The combination of free solution and gel electrophoretic separation experiments gives a plethora of information, such as the number and relative amounts of the components in a mixture. When the components are specifically identified, e.g., by antigen-antibody binding, unequivocal identification of the presence of the given component is afforded. As a consequence, electrophoresis has become the cornerstone of macromolecular analysis in biotechnology.

Traditional electrophoretic media are large in dimension, being on the order of mm. A recent development in the field of electrophoretic technology is high performance capillary electrophoresis. In accordance with this methodology the separation media are made of hollow fibers with an inner diameter of 25 to 100 microns. This separation configuration allows a high current to pass through the media in the hollow fiber. The Joule heating can be efficiently removed due to the small size of the capillary. As a result, sample analysis time is greatly reduced. However, such high performance electrophoresis still requires the use of a high voltage DC power supply (e.g., up to tens of kv) to accomplish separation. In addition, gel-filled capillaries are not commercially available and are difficult to make. The parallel idea in slab gel media involves the use of very thin slabs. Here, gel formation involves sufficient shrinkage, making the edges of the slab more stressed than the center. Hence, if the same sample is separated using both an edge and a center track, it will exhibit different resolved patterns. This is a major problem in slab gel electrophoresis. Here again, as in capillary electrophoresis, high voltage power supplies are needed and the resulting resolution (although the best available) is not entirely satisfactory.

In both capillary and slab electrophoresis, the field applied is fixed, thus passive. Although crossed field and pulsed field electrophoresis (2D electrophoresis) methods have been described, their application is limited. In all cases, the entire separation media, free solution or gel, are under the same applied field at a given time. The field may change temporally, but not spatially by design. Accordingly, the entire sample of charged particles to be separated are under the same field at any given time.

There is also an interest in being able to move small volumes in a rapid and efficient manner without electroendoosmotic mixing. By having a system whereby particular reactant solutions can be moved by electrokinetic forces, one can carry out reactions with small volumes and within a small space.

SUMMARY OF THE INVENTION

The present invention relates to moving charged particles such as charged molecules within a medium in response to a plurality of electrical fields which are applied simultaneously and/or sequentially along the medium containing the charged molecules in order to move the charged molecules in a precise and controlled fashion. The movement of the electrical fields can be accurately controlled both spatially and temporally. Charged particles in the medium can be moved so as to separate particular types of charged particles away from one another and thus provide a highly defined analytical technique. Further, specific charged molecules can be moved towards each other into precisely defined regions in order to react particular types of molecules together in a synthesis or sequencing protocol employing lateral branches to a central trench, where movement in the lateral branches is controlled by electrodes to provide for electrokinetic movement.

In accordance with one aspect of the invention, there is provided a charged particles moving device such as an electrophoresis device produced by any of a variety of procedures such as photolithography, silk-screening, laser, technologies, or vapor deposition which results in a patterning of electrical circuitry. In accordance with this device, there is provided a "movement area" which includes a medium in which the charged particles, such as charged molecules are to be moved. The movement area is positioned so that it can be continuously subjected to a plurality of electrical fields in a simultaneous or sequential manner. The electrical fields affecting the movement area are activated so as to move charged molecules in a controlled manner through the medium in the movement area. Accordingly, mixtures of different types of charged molecules can be separated away from each other in order to provide an analytical technique.

As a device for conducting reactions (e.g., sequencing synthesis methods), the different fields connected to the movement area can be applied so as to move specific types of charged molecules into contact with other types of charged molecules in order to react the molecules and carry out any number of different reaction protocols. The electrical connections contacting the movement area are preferably in the form of intelligent integrated circuitry which is interactive with a computer system capable of activating the fields in any given manner so as to create precise types of separation of molecules for analysis or combinations of molecules for reaction.

A primary object of the present invention is to provide a device which is capable of moving charged particles through a medium in a precise controlled fashion in response to a plurality of different electrical fields, which fields are preferably generating forces which vary in time and space simultaneously.

A feature of the present invention is that a plurality of different electrical fields are applied to a medium in order to move molecules within the medium in a precise manner.

Yet another advantage of the present invention is that devices of the invention can be efficiently and economically produced.

Yet another advantage of the present invention is the minimization or elimination of electroendosmosis by the utilization of polymeric substrates, such as polymethylmethacrylate.

Another feature of the devices of the present invention is the use of movement areas which have a cross-sectional shape which includes flattened or slab-like regions which regions allow for the efficient accurate use of spectrometer devices which can be used in connection with the invention.

Yet another feature of the invention is the inclusion of branched movement areas in which it is possible to move together and separate from each other charged particles in order to carry out complex reaction and/or separate schemes.

Yet another advantage of the present invention is the use of inert polymeric substrate materials or components which might contact charged particles to be separated or combined which materials minimize protein absorption and loss of sample materials being separated and/or combined.

These and other objects, advantages and features of the present invention will become apparent to those persons skilled in the art upon reading the details of the structure of the devices and methods of operation as more fully set forth below, reference being made to the accompanying drawings forming a part hereof.

DETAILED DESCRIPTION OF THE INVENTION

Before the present device and method for moving charged particles within a medium are described, it is to be understood that this invention is not limited to the particular component parts of the devices described or process steps of the methods described as such devices and methods may, of course, vary. It is also to be understood that the terminology used herein is for purposes of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a medium" includes one or more different media mixed together or separated from each other as well as different types of media known to those skilled in the art, reference to "an electrical field" includes a plurality of different electrical fields (of the type described) which may be applied in a number of different ways in order to obtain the effects of the type described herein, and reference to "the process step" includes any number of such steps which will be equivalent to the steps described herein and so forth.

Figure 1:
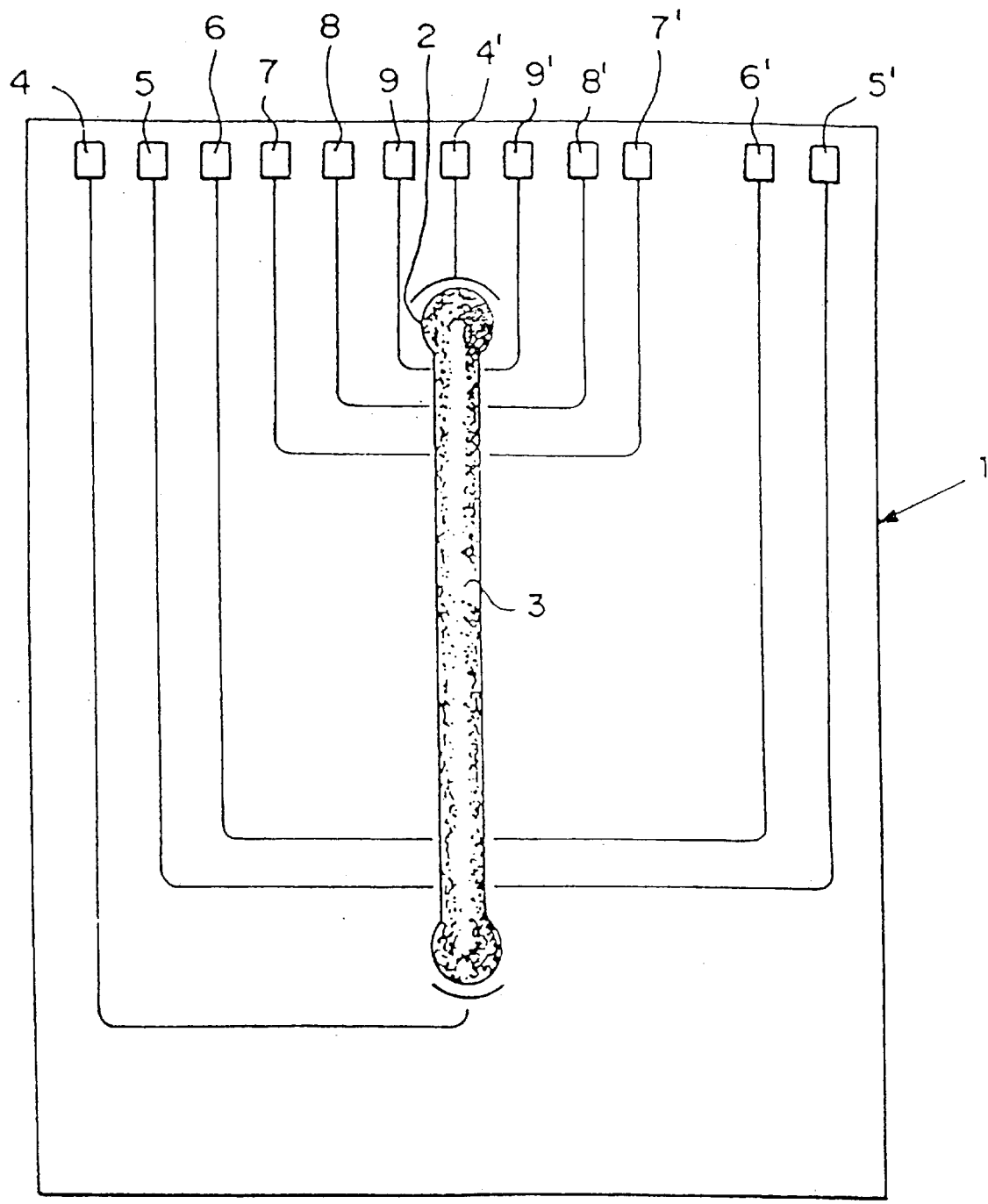
FIG. 1 is a plan front schematic view of a particular embodiment of the invention.

Referring now to the drawings, in FIG. 1, a specific embodiment of an analytical device useful in carrying out methods of the present invention is shown schematically. The device is on a Card 1 which may be comprised of a number of different types of materials such as various polymeric materials generally referred to as plastics. Further, the Card 1 may be in a variety of different sizes. For convenience, the card could be produced in the size of a conventional credit card.

The Card 1 includes a hollowed-out area or Trench 2 which, again, may be of any size but for convenience might preferably be produced on the credit card size Card 1 so that the Trench 2 is about 1–10 centimeters in length and has a depth of about 5–200, usually 5–150, particularly 5–25 microns. The cross-sectional shape (not shown) of the Trench 2 may vary and be rectangular, oval, circular or otherwise. It is preferably a flattened oval with the flat surface providing desired optical properties.

The Trench 2 is filled with a medium 3 which may be a buffer solution, polymeric solution, surfactant micellular dispersion or gel of the type generally used in connection with analytical separation techniques. For example, polyacrylamide gel used in PAGE analytical procedures is extremely useful in connection with the present invention. A variety of materials may be used alone or in combination with other materials which materials should provide frictional resistance to the charged particles and not substantially interfere with the electrical fields.

The Card 1 has plated thereon a plurality of electroplated finger-like electrodes 4–10. Only 7 electrodes are shown on the Card 1 for purposes of simplicity. However, photoelectroplating technology could be utilized to provide hundreds of different electrodes along the length of even a relatively small (1–10 cm) Trench 2. The electrodes can be spaced apart from each other at any given interval. In connection with this embodiment of the invention, there are preferably 400 to 800 electrodes and they are preferably placed at regular intervals approximately 1–100 microns apart. Some preferred embodiments of the device include 5–25 electrical fields, 50–100 electrical fields, and 500 to over 1000 electrical fields. The electrodes creating these fields may be placed apart from one another at a distance 0.01 to 10 centimeters, but are more preferably placed at a range of about 1–100 microns apart from each other.

The electrodes 4–10 are either simultaneously biased by the application of different voltages to each of the electrodes 4–10 or sequentially biased by the application of different voltages which are biased in a programmed manner. Since the spacing of the electrodes 4–10 is small, it is possible to attain relatively high field strength between the electrodes even while applying relatively low voltages. This is a substantial advantage of the present invention over prior art methods which utilize only one electrical field over the entire medium (having a large dimension) and thus require the application, of substantially large voltages.

The electrodes 4–10 are biased or fired simultaneously or sequentially and the magnitude of the field applied across any given electrode or all of the electrodes is adjustable over any given range at any given instant in time. The ability to activate the electrodes in any given fashion and apply different voltages across any given electrode gives rise to a greatly improved ability to separate molecules moving within the medium from each other in an extremely precise fashion, thus obtaining analytical resolution of different types of molecules to a degree far beyond that of conventional techniques.

The Card 1 as well as the Trench 2 and electrode connections 4–10 can be readily and economically produced by standard microelectronic fabrication techniques. Accordingly, multiple copies of nearly identical cards can be readily reproduced with a high degree of accuracy. The fidelity and economy of production are important features of the invention. Since the substrate of the card is preferably a rigid polymeric material, particularly synthetic organic polymers or plastics, addition or condensation polymers, such as polymethylmethacrylate, polycarbonate, polyethylene terepthalate, polystyrene or styrene copolymers, the card itself does not have a surface charge. Accordingly, there is no (or negligible) surface charge in the Trench 2, and therefore the problem of electroendosmosis is alleviated. Electroendosmosis is a substantial problem in connection with high performance capillary electrophoresis techniques which utilize glass capillaries which generally must be coated with a polymer in order to suppress the electroendosmosis. The polymer material can be made substantially non-porous. Accordingly, the charged particles such as proteins are not absorbed and loss of sample during separation is minimal.

The solid synthetic organic polymers which find use can be readily formed into a variety of forms,.one form being the card, but other forms may include slabs with trenches or channels, tubes, rods, sheets, capillaries, or the like. These polymers readily lend themselves to fabrication and modification, being capable of being molded with the appropriate trenches or having the trenches formed in the preformed substrate or the products may be extruded, for example, capillaries for capillary electrophoresis. Of particular interest are the acrylates, which have good clarity.

It is important to note that the gel-filled channel 2 on the Card 1 does not have to contain cross-linked gels tethered to the wall. This greatly relieves the stress formed during polymerization and cross-linking. The gels need not be tethered to the wall because only a small fraction of the gel 3 in the Trench 2 is under applied electrical field at any given time. Since only a small portion of the gel 3 in the Trench 2 is subjected to the field at a given moment the field does not extrude the gel 3 out of the Trench 2 in any fashion.

The Card 1 having the Trench 2 and electrode connections 4–10 thereon can be produced by a variety of different techniques known to those skilled in the art. In general, one method for producing such a device is as follows employing photolithography as employed with the production of microelectronic computer chips. First, a substrate support such as a polymethylmethacrylate card approximately the size of a conventional credit card is provided. The surface of the card itself is not electrically conducting nor is the card. On the card is first deposited a thin layer of an electrically conducting material. The coating may be applied by a variety of different techniques known to those skilled in the art and may be comprised of a variety of different types of materials provided they are capable of conducting electricity. The layer is preferably extremely thin on the order of 100 angstroms to a few microns of thickness. The electrically conducting layer is then coated with a layer of material which is both light-sensitive and non-conducting. Once the light-sensitive, non-conducting layer completely covers the electrically conducting layer, a mask is applied to the surface of the light-sensitive, non-conducting layer. After the mask covers the layer, it is exposed to light resulting in a pattern of portions of the light-sensitive material being solvent soluble and portions being solvent insoluble. The soluble portions are washed away and the exposed electrically conducting material etched away leaving traces of wires and connectors to the wires under the insoluble portion of the light sensitive material. The underlying electrically conducting material will provide the plurality of electrode connections to the Trench 2. By removing a portion of the insoluble material from the ends or connectors of the electrically conducting traces remaining from the electrically conducting layer, electrical connection can be made with the electrode connectors to the Trench 2. In addition the electrode traces are protected from wear and abrasion by the protective coating.

As will be apparent to those skilled in the art, the mask utilized in the above production procedure can be produced so as to provide hundreds of different electrode connections to the Trench 2. Further, rather than utilizing the photolithographic technique generally described above, it is possible to utilize other techniques such as employing various types of laser technologies and/or other technologies such as silk-screening and vapor deposition which make it possible to provide extremely small (in size) and large numbers of electrodes to the Trench 2. The greater the number of electrodes, the less voltage which needs to be supplied to each electrode and the more accurately it is possible to control the motion of the charged particles within the trench.

Once the card having the electrodes thereon is produced, the Trench 2 may be filled with a medium 3 which is preferably in the form of a polyacrylamide gel material or a buffered solution with or without a synthetic polymer; alone or in combination with a surfactant. In order to carry out the electrophoresis or movement of charged particles for synthesis or sequencing, a buffer will be supplied, at reservoirs at the termini of the trenches and lateral branches or means can be provided for connecting the ends of the trenches and lateral branches to reservoirs for allowing for the flow of liquid during operation of the device. After the gel has been added, a sample of material is then placed at one end of the medium and time-dependent and/or variable positiondependent voltages are applied to the electrodes. Although it is possible to supply the voltage to the electrodes in a variety of different manners, it is most preferable to supply the voltage so that electrical fields are sequentially activated one after another in a single direction so as to provide a traveling electrical wave which moves in a single direction along the trench. This wave or waves can be made to move at a variety of speeds depending upon the particular types of molecules being separated. As the wave or waves move, charged particles will be drawn through the medium within the Trench 2. Charged particles which tend to move more quickly will, of course, be drawn through the medium by moving waves which move quickly along the length of the trench. However, particles which tend to move slowly through the medium 3 can only be moved by waves which move generally slowly through the medium 3.

Although the above-described traveling electrical waves are the preferred method of carrying out the separation processing of the invention, similar separation and resolution capabilities can be obtained in another manner. For example, all of the electrodes positioned along the Trench 2 may be biased simultaneously but have different voltages depending on the electrode spacing and position of any given electrode. The voltages supplied to any given electrode may also be changed continuously over time so as to create different wave-like force affects on the charged particles within the medium and move the particles through the medium at different rates based on factors such as the size, shape and charge of the particles being moved through the medium.

The embodiment described above can be modified in a variety of different fashions. For example, it is possible for the electrodes to have opposing ends on either side of the Trench 2. If the device is constructed in this fashion, charged particles will be moved through the medium 3 in a zig-zag fashion as the different electrodes are activated.

In order to avoid the zig-zag movement of the charged particles through the medium 3, a variety of other embodiments are possible. For example, two cards can be produced wherein one card is substantially the mirror image of the other. The two cards are placed in facing abutment to each other so that the Trench 2 forms an enclosed column. In accordance with this embodiment, the electrode lines do not end at the edge of the Trench 2, but rather continue across the trench on both the top and the bottom. Thus, electrical potential will permeate around the column formed at a plurality of different spaced intervals along the column. By sequentially activating the electrodes, an electrical field wave is caused to move from one end of the column to the other. This creates an effect which draws charged particles through the medium within the column. Again, faster molecules are driven through the medium by moving waves which move quickly along the column and slower molecules will be moved through the medium by waves which move more slowly. By providing a plurality of different speeds of moving waves, it is possible to precisely resolve different bands or groups of charged particles within the medium.

Alternatively, the electrodes on the device may be fired simultaneously in accordance with a predetermined scheme which will create a complex voltage profile across the entire length of the column. The voltage profile will create forces on the charged particles within the column and can be changed over time in order to obtain precise resolution of different species or groups of charged particles within a sample being resolved.

Regardless of the embodiment of the invention which is constructed, it is preferable for the electrodes to be connected to an electronic computer which computer has programmed software dedicated to providing the moving waves or voltage profile along the Trench 2. Various different types of software can be provided so as to obtain the best possible resolution with respect to separating various types of charged particles from one another.

In yet a more sophisticated embodiment of the invention, the computer software which is connected to the electrodes can be made interactive with an optical detection device such as an ultraviolet or fluorescence spectrometer. The spectrometer can be focused singly or at various points along the medium 3 in the Trench 2. As the ultraviolet spectrometer reads different types of particles being moved to different portions of the medium 3, the information can be sent to the computer which can adjust the speed of the waves or voltage distribution profiles being generated in order to more precisely fine-tune the resolution of the charged particles being moved through the medium 3.

It will apparent to those skilled in the art that the Trench 2 can be in any shape. More specifically, the Trench 2 can be fashioned so that it has a plurality of branches thereon. Each of the branches of the Trench 2, along with the trench itself can be filled with a buffer solution. Thereafter, the base of each of the branches can be supplied with a particular charged reactant material. The charged reactant materials can then be moved into contact with one another by utilizing the moving electrical wave generated by the computer. Accordingly, sophisticated computer programs can be set up in order to provide for synthesis or sequencing protocols of a variety of different types of molecules. For example, different nucleotides can be reacted to form DNA and different amino acids can be reacted to form proteins. These reactions can be carried out at greatly increased speeds as compared with conventional mechanical technologies. In addition to increased speeds, the yield is vastly improved due to the precision with which the reactants can be moved.

In addition to carrying out synthesis reactions in a manner described above, it is possible to carry out DNA or protein sequencing procedures. In connection with these procedures, individual amino acids on proteins or individual nucleotides on DNA molecules can be successively cleaved from one end of the molecule. As the amino acid or nucleotide is cleaved, it can be moved to a given location within the device and identified such as by utilizing a spectrometer. The use of such a sequencing methodology obviates the need for valves, reagents, bottles, washing, filtration and many of the tedious operations which are mechanical in nature and necessary in connection with conventional sequencing methodologies.

In addition to the separation, synthesis and sequencing methods described above, the present invention is useful for a variety of additional purposes. For example, it is possible to utilize specific embodiments of the invention in order to separate impurities from large mixtures of compounds and thus carry out a purification processing which is substantially more refined than vacuum fractionization processing. A mixture of components can be separated into a variety of pure groups and moved along parallel tracks. Upon resolving the mixtures, the desired components can be guided by the electrical wave fields in lateral directions at a given precise moment in time and caused to react with a given neighboring reactant. Alternatively, selected components may be guided to trenches filled with antigen-antibodies reactive with given charged particles being moved in the medium or moved into contact with complementary components, dyes, fluorescent tags, radiotags, enzyme-specific tags or other types of chemicals for any number of purposes such as various transformations which are either physical or chemical in nature. Further, bacterial or mammalian cells, or viruses may be sorted by complicated trench networks which networks are in connection with a plurality of electrodes capable of generating fields in a variety of different ways in order to move the cells or viruses through the fields based on the size, charge or shape of the particular material being moved. Separated cells or viruses may be analyzed or modified subsequently.

Figure 2:
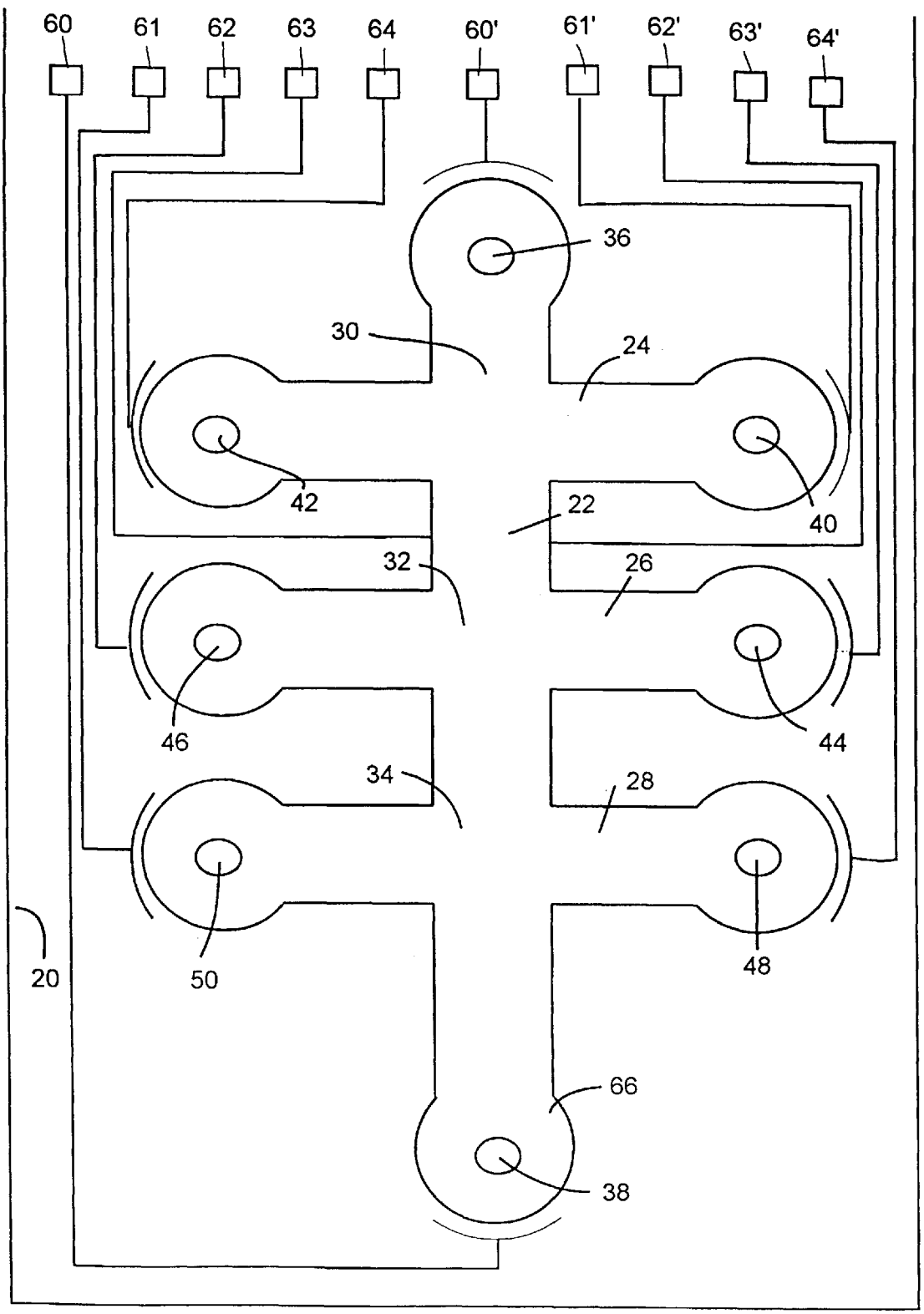
FIG. 2 is a plan schematic view of a second embodiment of the invention, providing a central trench and lateral branches with individual electrodes independently controlling the electrical fields in the trench and branches.

The embodiment in FIG. 2 provides for mixing and separation of molecules, so that reactions may be carried out between different reactants, mixtures separated and components combined with other materials, assays carried out by mixing a component of a sample with one or more assay reagents, and the like. In FIG. 2, Card 20 has a network which includes a central hollowed-out area or trench 22 with lateral hollowed areas or trenches serving as branches, with an upper branch 24, a middle branch 26 and a lower branch 28. The branches 24, 26 and 28 cross and interconnect with the central trench 22, forming reaction sites 30, 32 and 34, respectively. The central trench 22 has entry port 36 and exit port 38 for introduction and removal of samples, mixtures, reactants and the like. Each of the branches have similar ports, the upper branch 24, having entry and exit ports, 40 and 42, respectively, the middle branch entry and exit ports, 44 and 46, respectively, and the lower branch, 48 and 50, respectively. The ports 36 and 38 communicate with reservoirs 37 and 39, respectively. Similarly, reservoirs could be provided proximal to the ends of the branches, if desired. The reservoirs have sufficient capacity for performing the necessary operations and providing the necessary ions for movement of the components of interest during the operation. Alternatively, the reservoirs may be connected to pumps for pumping liquid into the reservoirs to maintain the reservoirs at a substantially constant composition.

The Card 20 has plated thereon a plurality of electroplated finger-like electrodes 60–64. The electrodes are biased in accordance with the needs of the purpose for which the Card 20 is being used. Thus, the electrodes 60 and 60' can be biased to move a sample from entry port 36 to reaction site 30. Once the sample is at or adjacent the reaction site 30, a reactant may be introduced into entry port 40 and by biasing electrodes 63 and 63', the reactant moved to the reaction site 30 to permit mixing and reaction at reaction site 30. By allowing the sample and reactant to incubate for sufficient time for reaction to occur, either under an appropriate electrical field or no field, one may then bias electrodes 60 and 60' to move the reacted sample down the central trench 22. The process of movement and reaction may be permitted at each reaction site, where depending upon the system, separation of the reaction mixture may result between reaction sites or all of the reaction mixture may be simultaneously moved to the next reaction site. If desired, components may be removed from the reaction mixture, where the reaction mixture has undergone separation between reaction sites. When a component reaches a reaction site, the electrodes controlling the branch may be activated to provide a bias which will move the component into the respective branch and out of the central trench 22. Finally, the reaction mixture may be moved to terminal site 66. Where a detectable label has been provided, as in an assay sequence, one may determine the signal from the label. Alternatively, one may withdraw the components of the reaction mixture through an appropriate port, not shown.

In addition to the electrodes controlling the central trench 22 and branches 24, 26 and 28, electrodes 63 and 63' are provided which provide for an electrical bias along the central trench, which electrodes may be used as described above or for moving sample and reactants in various directions by appropriately biasing individual electrodes, with different pairs of electrodes being used. For example, by appropriately biasing electrodes 61' and 63 one may bring a reactant into the central channel to the position where electrode 63 is placed. One may provide for a plurality of electrodes along the central trench 22, as described above, so that fine control of movement of the components present in the central trench and branches may be attained.

While the present invention has been described with reference to specific embodiments, it should be understood by those skilled in the art that obvious changes may be made and equivalents may be substituted without departing from the true spirit and scope of the invention. In addition, many modifications may be made to adapt the methods and devices of the present invention to particular situations, materials, compositions of matter, processes, process step or steps, to the objective, spirit and scope of the present invention. All such modifications are intended to be within the scope of the claims appended hereto.

What is claimed is:

1. A method for carrying out a chemical reaction comprising:

adding charged reactant materials to one or more channels in a chemical-reaction device, said device comprising an electrically non-conductive support having an upper surface, a main channel in said solid support extending downward from said upper surface, a plurality of branch channels connected to said main channel, conductive media contained in said channels, and a plurality of electrodes in contact with said media;

electrophoretically moving said materials by supplying electrical potentials across selected electrodes in the device whereby said materials are brought into contact with each other and react.

2. The method of claim 1 wherein one or more of said materials comprises a nucleotide.

3. The method of claim 2 wherein said reaction is the sequencing of DNA.

4. The method of claim 2 wherein said reaction is the synthesis of DNA.

5. The method of claim 4 wherein said reaction is the sequencing of DNA.

6. The method of claim 4 wherein said reaction is the synthesis of DNA.

7. The method of claim 4 wherein said reaction is the sequencing of a protein.

8. The method of claim 4 wherein said reacetion is the synthesis of a protein.

* * * * *